(12) United States Patent
Tsujioka et al.

(10) Patent No.: US 6,849,752 B2
(45) Date of Patent: Feb. 1, 2005

(54) PROCESS FOR SYNTHESIZING IONIC METAL COMPLEX

(75) Inventors: Shoichi Tsujioka, Saitama (JP); Hironari Takase, Saitama (JP); Mikihiro Takahashi, Saitama (JP); Yoshimi Isono, Saitama (JP)

(73) Assignee: Central Glass Company, Ltd., Ube (JP)

( * ) Notice: Subject to any disclaimer, the term of this patent is extended or adjusted under 35 U.S.C. 154(b) by 0 days.

(21) Appl. No.: 10/285,680

(22) Filed: Nov. 1, 2002

(65) Prior Publication Data

US 2003/0100761 A1 May 29, 2003

(30) Foreign Application Priority Data

Nov. 5, 2001 (JP) ........................................ 2001-339630
Jan. 18, 2002 (JP) ........................................ 2002-009342

(51) Int. Cl.[7] .............................. C07F 5/02; C07F 7/02; C07F 9/02
(52) U.S. Cl. ............................... 556/41; 556/40; 568/6; 568/12; 568/14; 534/15
(58) Field of Search ...................... 556/40, 41; 534/15; 568/6, 12, 14

(56) References Cited

U.S. PATENT DOCUMENTS 6,407,232 B1 * 6/2002 Tsujioka et al. .............. 544/54
6,485,868 B1 * 11/2002 Tsujioka et al. ............. 429/306
6,506,516 B1 * 1/2003 Wietelmann et al. ....... 429/188
6,783,896 B2 * 8/2004 Tsujioka et al. ............. 429/306

FOREIGN PATENT DOCUMENTS

| CA | 2 379 985 A1 * | 2/2001 |
| DE | 198 29 030 | 10/1999 |
| DE | 199 33 898 | 2/2001 |
| EP | 1 074 555 | 2/2001 |
| EP | 1 075 036 | 2/2001 |
| EP | 1195834 | 4/2002 |

OTHER PUBLICATIONS

Balkus et al., "Tris(oxaloto) Complexes of Silicon as Precursors to Porous Silicate Materials: Synthesis and Structure", *Inorganic Chemistry*, vol. 34 (1995), pp. 5776–5780.
Specification of 09/969,127 filed on Oct. 3, 2001.

* cited by examiner

*Primary Examiner*—Porfirio Nazario-Gonzalez
(74) *Attorney, Agent, or Firm*—Crowell & Moring LLP

(57) ABSTRACT

The invention relates to a process for synthesizing an ionic metal complex represented by the general formula (1) or (5). This process includes reacting in an organic solvent a compound (corresponding to ligand of the complex) represented by the general formula (2) or (6) with a halogen-containing compound represented by the general formula (3) or (4), in the presence of a reaction aid containing an element selected from the group consisting of elements of groups 1–4 and 11–14 of the periodic table. It is possible by this process to easily and efficiently synthesize the ionic metal complex, which can be used as a supporting electrolyte for electrochemical devices, a polymerization catalyst of polyolefins and so forth, or a catalyst for organic synthesis.

24 Claims, No Drawings

PROCESS FOR SYNTHESIZING IONIC METAL COMPLEX

BACKGROUND OF THE INVENTION

The present invention relates to a process for synthesizing an ionic metal complex that can be used as a supporting electrolyte for lithium batteries, lithium ion batteries, electrical double-layer capacitors and other electrochemical devices, a polymerization catalyst for polyolefins and so forth, or a catalyst for organic synthesis.

Ionic complexes, such as $PF_6^-$, $BF_4^-$ and $AsF_6^-$, formed by bonding of Lewis acids with F ion have been used in applications such as supporting electrolytes for electrochemical devices, polymerization catalysts for polyolefins and so forth or catalysts for organic synthesis due to their solubility and ion dissociation characteristics and their high activity in reactions.

As the application range of these ionic complexes becomes increasingly diverse, efforts are being made to search for the optimum ionic complex for each application, and these ionic complexes are being required to have properties including heat resistance, hydrolysis resistance, low toxicity and recycleability. Under such condition, there have been proposed many complexes in which an organic ligand is bonded to the central element, in addition to conventional complexes in which a simple element (e.g., fluorine and oxygen) as a ligand is bonded to the central element.

There are various processes for synthesizing ionic complexes. For example, it is possible to use a neutralization reaction between (a) a hydroxide of an element corresponding to the central element and (b) a ligand having an active hydrogen of a high acidity. As another example, it is possible to use a desalting reaction between (a) a halide of an element corresponding to the central element and (b) a ligand (e.g., alkali metals) having high degree of dissociation. Depending on the combination of ligand and central element, however, reactivity may become too low to synthesize ionic complexes. Thus, it may become difficult to obtain the originally designed complexes.

SUMMARY OF THE INVENTION

It is an object of the present invention to provide a process for easily and efficiently synthesizing an ionic metal complex.

According to the present invention, there is provided a first process for synthesizing an ionic metal complex represented by the general formula (1). The first process comprises reacting in an organic solvent a compound represented by the general formula (2) with a halogen-containing compound represented by the general formula (3) or (4), in the presence of a reaction aid comprising an element selected from the group consisting of elements of groups 1–4 and 11–14 of the periodic table,

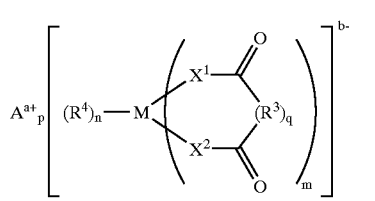
(1)

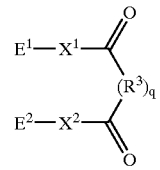
(2)

$$A^{a+}{}_p[(R^4)_n\!-\!M\!-\!\!(\!R^8)\!)_{2m}]^{b-} \quad (3)$$

$$(R^4)_n\!-\!M\!-\!\!(\!R^8)\!)_{2m-1} \quad (4)$$

According to the present invention, there is provided a second process for synthesizing an ionic metal complex represented by the general formula (5). The second process comprises reacting in an organic solvent a compound represented by the general formula (6) with a halogen-containing compound represented by the general formula (3) or (4), in the presence of a reaction aid comprising an element selected from the group consisting of elements of groups 1–4 and 11–14 of the periodic table,

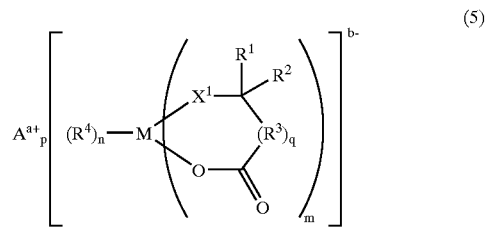
(5)

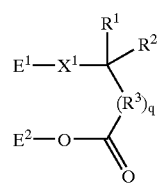
(6)

In the general formulas (1) to (6), M represents a transition metal selected from the group consisting of elements of groups 3–11 of the periodic table, or an element selected from the group consisting of elements of groups 12–15 of the periodic table;

$A^{a+}$ represents a metal ion, hydrogen ion or onium ion;

a represents a number from 1 to 3; b represents a number from 1 to 3; p is b/a; m represents a number from 1 to 4; n represents a number from 0 to 8; q is 0 or 1;

each of $R^1$ and $R^2$ independently represents a hydrogen, halogen, $C_1$–$C_{10}$ alkyl group, or $C_1$–$C_{10}$ halogenated alkyl group;

$R^3$ represents a $C_1$–$C_{10}$ alkylene group, $C_1$–$C_{10}$ halogenated alkylene group, $C_4$–$C_{20}$ arylene group or $C_4$–$C_{20}$ halogenated arylene group, these alkylene and arylene groups of the $R^3$ optionally having substituents and hetero atoms, one of the $R^3$ being optionally bonded with another of the $R^3$;

$R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$, these alkyl and aryl groups of the $R^4$ optionally having substituents and hetero atoms, one of the $R^4$ being optionally bonded with another of the $R^4$ to form a ring;

each of $X^1$, $X^2$ and $X^3$ independently represents O, S, $NR^5$ or $NR^5R^6$;

each of $R^5$, $R^6$ and $R^7$ independently represents a hydrogen, $C_1$–$C_{10}$ alkyl group, $C_1$–$C_{10}$ halogenated alkyl group, $C_4$–$C_{20}$ aryl group, or $C_4$–$C_{20}$ halogenated aryl group, these alkyl and aryl groups of the $R^5$, $R^6$ and $R^7$ optionally having substituents and hetero atoms, one of the $R^5$ being optionally bonded with another of the $R^5$ to form a ring, one of the $R^6$ being optionally bonded with another of the $R^6$ to form a ring, one of the $R^7$ being optionally bonded with another of the $R^7$ to form a ring;

each of $E^1$ and $E^2$ independently represents hydrogen or an alkali metal; and $R^8$ represents a halogen.

DESCRIPTION OF THE PREFERRED EMBODIMENTS

In the above general formulas, M is selected from elements of groups 3–15 of the periodic table. It is preferably Al, B, V, Ti, Si, Zr, Ge, Sn, Cu, Y, Zn, Ga, Nb, Ta, Bi, P, As, Sc, Hf or Sb.

$A^{a+}$ is a metal ion, hydrogen ion or onium ion. Preferably, $A^{a+}$ is a lithium ion, quaternary alkylammonium ion or hydrogen ion. Specific examples of $A^{a+}$ include lithium ion, sodium ion, potassium ion, magnesium ion, calcium ion, barium ion, cesium ion, silver ion, zinc ion, copper ion, cobalt ion, iron ion, nickel ion, manganese ion, titanium ion, lead ion, chromium ion, vanadium ion, ruthenium ion, yttrium ion, lanthanoid ion, actinoid ion, tetrabutylammonium ion, tetraethylammonium ion, tetramethylammonium ion, triethylmethylammonium ion, triethylammonium ion, pyridinium ion, imidazolium ion, hydrogen ion, tetraethylphosphonium ion, tetramethylphosphonium ion, tetraphenylphosphonium ion, triphenylsulfonium ion, triethylsulfonium ion and triphenylmethyl ion.

Valency (valence) of the $A^{a+}$ cation is preferably from 1 to 3. If the valency is larger than 3, the problem occurs in which it becomes difficult to dissolve the ionic metal complex in solvent due to the increase in crystal lattice energy. Consequently, in the case of requiring solubility of the ionic metal complex, a valency of 1 is preferable. As shown in the general formulas (1) and (5), the valency (b$^-$) of the anion is similarly preferably from 1 to 3, and a valency of 1 is particularly preferable. The constant p expresses the ratio of the valency of the anion to the valency of the cation, namely b/a.

In the above general formulas, $R^3$ is selected from $C_1$–$C_{10}$ alkylene groups, $C_1$–$C_{10}$ halogenated alkylene groups, $C_4$–$C_{20}$ arylene groups and $C_4$–$C_{20}$ halogenated arylene groups. These alkylene and arylene groups may have substituents and hetero atoms in their structures. For example, the alkylene and arylene groups may have structures in which hydrogen has been replaced with a substituent selected from halogens, chain-like or cyclic alkyl groups, aryl groups, alkenyl groups, alkoxy groups, aryloxy groups, sulfonyl groups, amino groups, cyano groups, carbonyl groups, acyl groups, amide groups, hydroxyl group and oxo group (=O). Furthermore, they may have structures in which carbon has been replaced with a substituent selected from nitrogen, sulfur and oxygen. When $R^3$ exist in the plural number, they may be bonded together. For example, a ligand such as ethylenediaminetetraacetic acid can be cited.

$R^3$ is preferably one that forms a 5 to 10-membered ring when a chelate ring is formed with the central M. The case of a ring having more than 10 members is not preferable, since advantageous chelating effects are reduced. In addition, in the case that $R^3$ has a portion of hydroxyl group or carboxyl group, it is possible to form a bond between the central M and this portion.

In the above general formulas, $R^4$ is selected from halogens, $C_1$–$C_{10}$ alkyl groups, $C_1$–$C_{10}$ halogenated alkyl groups, $C_4$–$C_{20}$ aryl groups, $C_4$–$C_{20}$ halogenated aryl groups and $X^2R^7$. Similar to $R^3$, these alkyl and aryl groups may have substituents and hetero atoms in their structures. When $R^4$ exist in the plural number, they may be bonded together to form a ring. $R^4$ is preferably an electron attracting group, particularly fluorine. When $R^4$ is fluorine, the degree of dissociation of the electrolyte is improved due to its strong electron attraction. Furthermore, mobility of the electrolyte is also improved due to the reduced size of the anionic moiety of the electrolyte. Therefore, the ionic conductivity becomes very high when $R^4$ is fluorine.

As mentioned above, each of $X^1$, $X^2$ and $X^3$ in the above general formulas independently represents O, S, $NR^5$ or $NR^5R^6$. Thus, the ligands are bonded to M with an interposal of these hetero atoms (O, S and N) therebetween. Although the bonding of an atom other than O, S or N is not impossible, the synthesis becomes extremely bothersome.

The ionic metal complex represented by the general formula (1) is characterized by these ligands forming a chelate structure with M since there is bonding with M by $X^1$ and $X^3$ within the same ligand. As a result of this chelation, the heat resistance, chemical stability and hydrolysis resistance of the ionic metal complex are improved. Although constant q in this ligand is either 0 or 1, in the case of 0 in particular, since the chelate ring becomes a five-member ring, chelating effects are demonstrated most prominently, making this preferable due to the resulting increase in stability.

In the above general formulas, each of $R^5$, $R^6$ and $R^7$ independently represents a hydrogen, $C_1$–$C_{10}$ alkyl group, $C_1$–$C_{10}$ halogenated alkyl group, $C_4$–$C_{20}$ aryl group, or $C_4$–$C_{20}$ halogenated aryl group. These alkyl and aryl groups optionally have substituents and hetero atoms. When $R^5$, $R^6$ and $R^7$ are each exist in the plural number, each of $R^5$, $R^6$ and $R^7$ may be formed into a ring.

Each of $R^5$ and $R^6$ differs from other groups (e.g., $R^1$ and $R^2$) in that the former is not required to be an electron attracting group. In the case of introducing an electron attracting group as $R^5$ or $R^6$, the electron density on N of $NR^5R^6$ decreases, thereby preventing coordination on the central M.

$R^7$ is preferably a $C_1$–$C_{10}$ fluorinated alkyl group. Due to the presence of an electron-attracting halogenated alkyl group as $R^7$, the negative charge of the central M is dissipated. Since this increases the electrical stability of the anion of the general formula (1) or (5), ion dissociation becomes extremely easy resulting in an increase of the ionic metal complex in solvent solubility, ion conductivity and catalyst activity. In addition, other properties of heat resistance, chemical stability and hydrolysis resistance are also improved. The case in which the halogenated alkyl group as $R^7$ is a fluorinated alkyl group in particular results in even greater advantageous effects.

For example, the alkyl and aryl groups of $R^7$ may have structures in which hydrogen has been replaced with a substituent selected from halogens, chain-like or cyclic alkyl groups, aryl groups, alkenyl groups, alkoxy groups, aryloxy groups, sulfonyl groups, amino groups, cyano groups, carbonyl groups, acyl groups, amide groups, hydroxyl group and oxo group (=O). Furthermore, they may have structures in which carbon has been replaced with a substituent selected from nitrogen, sulfur and oxygen.

In the above general formulas, the values of the constants m and n relating to the number of the above-mentioned ligands depend on the type of the central M. In fact, m is preferably from 1 to 4, while n is preferably from 0 to 8.

Specific examples of the ionic metal complex represented by the general formula (1) are as follows.

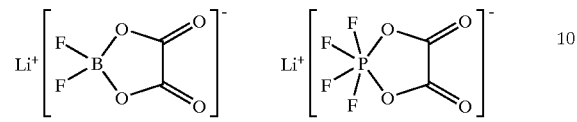

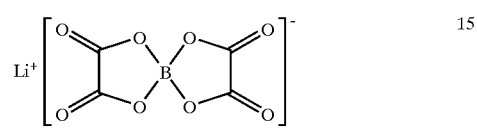

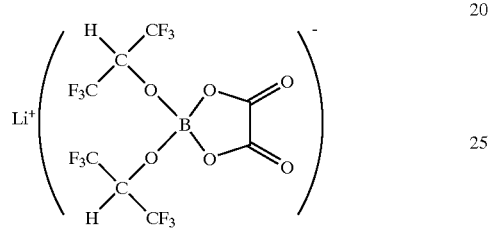

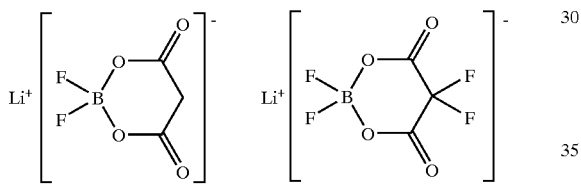

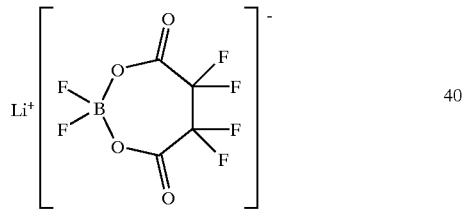

In the general formulas (5) and (6), each of $R^1$ and $R^2$ is independently selected from H, halogen, $C_1$–$C_{10}$ alkyl groups and $C_1$–$C_{10}$ halogenated alkyl groups. At least one of $R^1$ and $R^2$ is preferably a fluorinated alkyl group, and more preferably, at least one of $R^1$ and $R^2$ is a trifluoromethyl group. Due to the presence of an electron-attracting halogen and/or a halogenated alkyl group for $R^1$ and $R^2$, the negative charge of the central M is dissipated. This results in an increase of the anion of the general formula (5) in electrical stability. With this, the ion dissociation becomes extremely easy resulting in an increase of the ionic metal complex in solvent solubility, ion conductivity, catalyst activity and so forth. In addition, other properties of heat resistance, chemical stability and hydrolysis resistance are also improved. The case in which the halogen is fluorine in particular has significant advantageous effects, while the case of a trifluoromethyl group has the greatest advantageous effect.

Specific examples of the ionic metal complex represented by the general formula (5) are as follows.

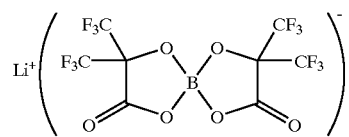

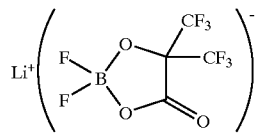

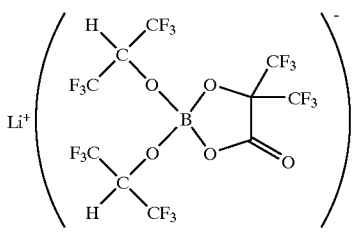

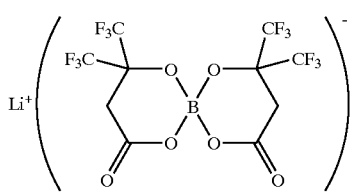

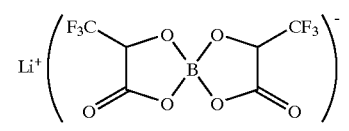

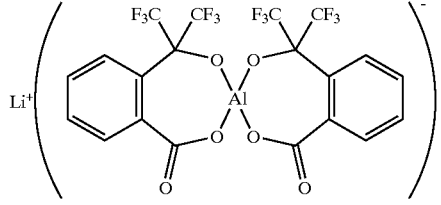

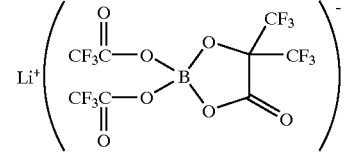

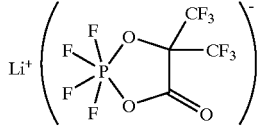

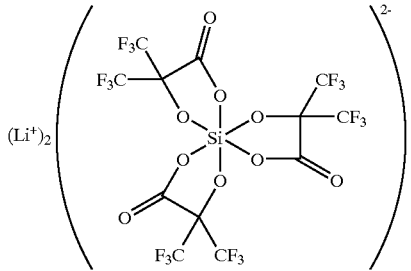

-continued

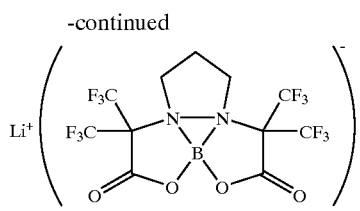

The first or second process for synthesizing the ionic metal complex according to the present invention will be further explained in the following. The first or second process is characterized in that a compound represented by the general formula (2) or (6) (corresponding to ligand of the complex) is reacted with a halogen-containing compound represented by the general formula (3) or (4) (a source of the central element M of the complex) in an organic solvent in the presence of a special reaction aid.

The compound represented by the general formula (2) or (6) contains $E^1$ and $E^2$ each independently being an active hydrogen or alkali metal, for bonding the halogen $R^8$ of the halogen-containing compound with $E^1$ and $E^2$ and then for eliminating the halogen $R^8$. This compound may be classified as an alcohol, metal alkoxide, carboxylic acid, carboxylate, sulfonic acid, sulfonate, sulfinic acid, or sulfinate.

In the halogen-containing compound, at least one halogen is bonded with the central element M. In fact, this central element may be bonded with only halogens or with at least one halogen and at least one other substituent. $R^8$ is preferably fluorine. Specific examples of the halogen-containing compound are $LiPF_6$, $LiBF_4$, $LiAlCl_4$, $LiPF_3(CF_3)_3$, $LiBF_3$ (Ph), $BF_3$, and $PF_5$, where Ph represents a phenyl group.

As stated above, the reaction aid used in the first and second processes contains an element selected from the group consisting of elements of groups 1–4 and 11–14 of the periodic table, preferably the elements being Al, B, Si, alkali metals and alkali earth metals. Due to a strong bond between the element of the reaction aid and the halogen, the reaction aid can accelerate the reactions of the first and second processes. The reaction aid is a compound preferably selected from chlorides, bromides, iodides, alkoxides and carboxy compounds, more preferably selected from $AlCl_3$, $BCl_3$ and $SiCl_4$.

When the compound represented by the general formula (2) or (6) (hereinafter the compound (2) or (6); other compounds may also be referred to similarly) is mixed with the halogen-containing compound (3) or (4), small amounts of $E^1R^8$ and $E^2R^8$ (by-products) are generated. It is possible to remove these $E^1R^8$ and $E^2R^8$ by the reaction aid. With this, the chemical equilibrium of the reactions of the first and second processes changes towards the production of the target product. In other words, the reaction aid can accelerate these reactions. It is preferable to suitably select the compound (2) or (6) (corresponding to the ligand of the complex), the halogen-containing compound (3) or (4) (a source of the central atom M) and the reaction aid such that the by-products are smoothly precipitated or smoothly removed as a high-vapor-pressure component from the system.

Relative amounts of the reagents used in the reactions of the first and second processes are not particularly limited. It is possible to use the compound (2) or (6) in an amount of 1–8 moles and the reaction aid in an amount of 0.1–10 moles, per mol of the halogen-containing compound (3) or (4).

It is preferable to use a solvent in the reactions of the first and second processes. This solvent is preferably one that is capable of dissolving at least very small amounts of the raw materials and that does not react with the compounds in the system. It is more preferable that such solvent has a dielectric constant of 2 or greater. It is not preferable to use a solvent having no such dissolving capacity, since such solvent lowers the reaction rate. The reactions can proceed very smoothly by using a solvent that is capable of dissolving at least very small amounts of the raw materials, since the target ionic metal complexes (1) and (5) have very high solubilities. The solvent can be selected from carbonates, esters, ethers, lactones, nitriles, amides, sulfones, alcohols, aromatic compounds, and mixtures of these. Its specific examples are propylene carbonate, ethylene carbonate, diethyl carbonate, dimethyl carbonate, methyl ethyl carbonate, dimethoxyethane, acetonitrile, propionitrile, tetrahydrofuran, 2-methyltetrahydrofuran, dioxane, nitromethane, N,N-dimethylformamide, dimethylsulfoxide, sulfolane, γ-butyrolactone, toluene, ethanol, and methanol.

The reaction temperature of the first and second processes may be in a range of −80 to 100° C., preferably 0 to 80° C. The reaction may not proceed sufficiently with a reaction temperature lower than −80° C. The solvent and the raw materials may be decomposed with a reaction temperature higher than 100° C. The reaction can proceed with a sufficient reaction rate without no such decomposition, if the reaction temperature is in a range of 0 to 80° C.

Some of the raw materials used in the first and second processes may have a property to be hydrolyzed. Therefore, it is preferable to conduct the first and second processes in an atmosphere (e.g., air, nitrogen and argon) of low moisture content.

It is possible to purify the ionic metal complex, for example, by a recrystallization in which the reaction solution is concentrated to precipitate the crystals or by a reprecipitation in which a large amount of a poor solvent is added to the reaction solution and then by washing the resulting solid.

The following nonlimitative examples are illustrative of the present invention. Examples 1-1 to 1-6 are illustrative of the first process of the present invention, and Examples 2-1 to 2-4 are illustrative of the second process of the present invention.

EXAMPLE 1-1

In a glove box having an atmosphere of a dew point of −50° C., 1.31 g of oxalic acid, 1.37 g of lithium tetrafluoroborate ($LiBF_4$), and 20 ml of dimethylcarbonate were mixed together, followed by stirring sufficiently. With this, lithium tetrafluoroborate was dissolved completely, but oxalic acid was not. Therefore, the mixture became in the form of slurry. Then, 1.38 g of silicon tetrachloride (reaction aid) were slowly added to the mixture at room temperature with stirring. At the same time when this addition was started, a gas was generated violently. With this, the undissolved oxalic acid was dissolved, and the reaction proceeded. After the addition of silicon tetrachloride, stirring was continued for 3 hr. It was judged that the reaction had terminated by confirming that the generation of the gas stopped completely. Dimethyl carbonate was removed from the resulting reaction liquid at 40° C. under a reduced pressure of 133 Pa, thereby obtaining 2.09 g of a white solid as a product. This product was washed with 20 ml of dimethyl ether, followed by solid separation with filtration and then drying of the filtrate at 120° C. for 24 hr under a reduced pressure of 133 Pa, thereby obtaining 2.09 g of lithium difluoro(oxalato)borate (yield: 99.5%) represented by the following formula.

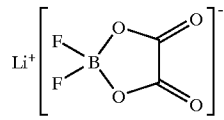

EXAMPLE 1-2

In a glove box having an atmosphere of a dew point of −50° C., 1.31 g of oxalic acid, 1.37 g of lithium tetrafluoroborate (LiBF$_4$), and 20 ml of dimethylcarbonate were mixed together, followed by stirring sufficiently. With this, lithium tetrafluoroborate was dissolved completely, but oxalic acid was not. Therefore, the mixture became in the form of slurry. Then, 1.30 g of aluminum trichloride (reaction aid) were slowly added to the mixture at room temperature with stirring. At the same time when this addition was started, a precipitate of a milky color was generated. After the addition of aluminum trichloride, stirring was continued for 3 hr. Then, the precipitate was separated from the reaction liquid by filtration. Dimethyl carbonate was removed from the resulting reaction liquid at 40° C. under a reduced pressure of 133 Pa, thereby obtaining 2.09 g of lithium difluoro(oxalato)borate (yield: 99.5%).

EXAMPLE 1-3

In a glove box having an atmosphere of a dew point of −50° C., 3.93 g of oxalic acid, 1.37 g of lithium tetrafluoroborate (LiBF$_4$), 0.76 g of lithium fluoride, and 50 ml of ethyl methyl carbonate were mixed together, followed by stirring sufficiently. With this, lithium tetrafluoroborate was dissolved completely, but oxalic acid and lithium fluoride were not. Therefore, the mixture became in the form of slurry. Then, 3.03 g of trimethoxyborane ((CH$_3$O)$_3$B; reaction aid) were slowly added to the mixture at 0° C. with stirring. At the same time when this addition was started, the undissolved component started to dissolve. At the time when all the reagents were dissolved after the addition of trimethoxyborane, ethyl methyl carbonate was removed from the resulting reaction liquid at 0° C. under a reduced pressure of 133 Pa, thereby obtaining 6.28 g of lithium difluoro(oxalato)borate (yield: 99.9%).

EXAMPLE 1-4

In a glove box having an atmosphere of a dew point of −50° C., 3.93 g of oxalic acid, 1.37 g of lithium tetrafluoroborate (LiBF$_4$), 0.76 g of lithium fluoride, and 50 ml of ethyl methyl carbonate were mixed together, followed by stirring sufficiently. With this, lithium tetrafluoroborate was dissolved completely, but oxalic acid and lithium fluoride were not. Therefore, the mixture became in the form of slurry. Then, 3.43 g of boron trichloride (BCl$_3$; reaction aid) were slowly added to the mixture at 0° C. with stirring. At the same time when this addition was started, the undissolved component started to dissolve and HCl gas started to form. At the time when all the reagents were dissolved after the addition of trimethoxyborane, ethyl methyl carbonate was removed from the resulting reaction liquid at 30° C. under a reduced pressure of 133 Pa, thereby obtaining 6.28 g of lithium difluoro(oxalato)borate (yield: 99.9%).

EXAMPLE 1-5

In a glove box having an atmosphere of a dew point of −50° C., 1.31 g of oxalic acid, 2.21 g of lithium hexafluorophosphate (LiPF$_6$), and 20 ml of diethyl ether were mixed together, followed by stirring sufficiently. With this, oxalic acid and lithium hexafluorophosphate were dissolved completely. Then, 1.38 g of silicon tetrachloride (reaction aid) were slowly added to the mixture at room temperature with stirring. At the same time when this addition was started, a gas was generated violently and the reaction proceeded. After the addition of silicon tetrachloride, stirring was continued for 5 hr. It was judged that the reaction had terminated by confirming that the generation of the gas stopped completely and by confirming with NMR that the raw materials disappeared. The obtained reaction liquid was filtrated, and then diethyl ether was removed from the resulting filtrate at 60° C. under a reduced pressure of 133 Pa, thereby obtaining 2.93 g of lithium tetrafluoro(oxalato)phosphate represented by the following formula.

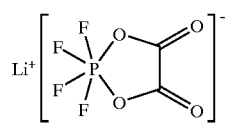

EXAMPLE 1-6

In a glove box having an atmosphere of a dew point of −50° C., 2.62 g of oxalic acid, 1.37 g of lithium tetrafluoroborate (LiBF$_4$), and 50 ml of γ-butyrolactone were mixed together, followed by stirring sufficiently. With this, lithium tetrafluoroborate and oxalic acid were dissolved completely. Then, 2.75 g of silicon tetrachloride (reaction aid) were slowly added to the mixture at room temperature with stirring. At the same time when this addition was started, a gas was generated violently and the reaction proceeded. After the addition of silicon tetrachloride, stirring was continued for 3 hr. It was judged that the reaction had terminated by confirming that the generation of the gas stopped completely. Then, γ-butyrolactone was removed from the resulting reaction liquid at 60° C. under a reduced pressure of 133 Pa, thereby obtaining a white solid as a product. This product was washed with 50 ml of dimethyl carbonate, followed by solid separation with filtration and then drying of the filtrate at 120° C. for 24 hr under a reduced pressure of 133 Pa, thereby obtaining 2.81 g of lithium bis(oxalato)borate (yield: 99.3%) represented by the following formula.

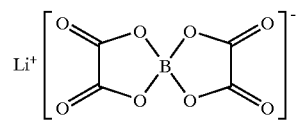

EXAMPLE 2-1

In a glove box having an atmosphere of a dew point of −50° C., 3.09 g of hexafluoro-2-hydroxyisobutyric acid (HOC(CF$_3$)$_2$COOH), 1.37 g of lithium tetrafluoroborate (LiBF$_4$), and 20 ml of dimethyl carbonate were mixed together, followed by stirring sufficiently to dissolve the reagents. Then, 1.38 g of silicon tetrachloride (reaction aid) were slowly added to the mixture at room temperature with stirring. At the same time when this addition was started, a gas was generated violently and the reaction proceeded. After the addition of silicon tetrachloride, stirring was continued for 3 hr. It was judged that the reaction had terminated by confirming that the generation of the gas stopped completely. Dimethyl carbonate was removed from the resulting reaction liquid at 60° C. under a reduced pressure of 133 Pa, thereby obtaining 3.87 g of a white solid as a product. This product is a lithium borate derivative represented by the following formula.

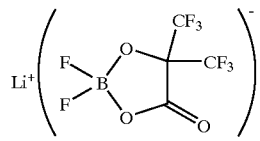

EXAMPLE 2-2

In a glove box having an atmosphere of a dew point of −50° C., 3.09 g of hexafluoro-2-hydroxyisobutyric acid (HOC(CF$_3$)$_2$COOH), 1.37 g of lithium tetrafluoroborate (LiBF$_4$), and 20 ml of diethyl carbonate were mixed together, followed by stirring sufficiently to dissolve the reagents. Then, 1.30 g of aluminum trichloride (reaction aid) were slowly added to the mixture at room temperature with stirring. At the same time when this addition was started, a precipitate of a milky color was generated. After the addition of aluminum trichloride, stirring was continued for 3 hr. Then, the precipitate was separated from the reaction liquid by filtration. Diethyl carbonate was removed from the resulting reaction liquid at 80° C. under a reduced pressure of 133 Pa, thereby obtaining 3.79 g of the same lithium borate derivative as that of Example 2-1.

EXAMPLE 2-3

In a glove box having an atmosphere of a dew point of −50° C., 3.08 g of hexafluoro-2-hydroxyisobutyric acid (HOC(CF$_3$)$_2$COOH), 2.21 g of lithium hexafluorophosphate (LiPF$_6$), and 20 ml of dimethyl carbonate were mixed together, followed by stirring sufficiently to dissolve the reagents. Then, 1.38 g of silicon tetrachloride (reaction aid) were slowly added to the mixture at room temperature with stirring. At the same time when this addition was started, a gas was generated violently and the reaction proceeded. After the addition of silicon tetrachloride, stirring was continued for 5 hr. It was judged that the reaction had terminated by confirming that the generation of the gas stopped completely and by confirming with NMR that the raw materials disappeared. The obtained reaction liquid was filtrated, and the resulting filtrate was dried at 60° C. under a reduced pressure of 133 Pa, thereby obtaining 2.93 g of a lithium phosphate derivative represented by the following formula.

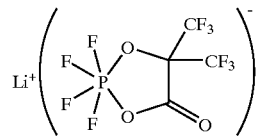

EXAMPLE 2-4

In a glove box having an atmosphere of a dew point of −50° C., 6.18 g of hexafluoro-2-hydroxyisobutyric acid (HOC(CF$_3$)$_2$COOH), 1.37 g of lithium tetrafluoroborate (LiBF$_4$), and 50 ml of acetonitrile were mixed together, followed by stirring sufficiently to dissolve the reagents.

Then, 2.75 g of silicon tetrachloride (reaction aid) were slowly added to the mixture at room temperature with stirring. At the same time when this addition was started, a gas was generated violently and the reaction proceeded. After the addition of silicon tetrachloride, stirring was continued for 3 hr. It was judged that the reaction had terminated by confirming that the generation of the gas stopped completely. Acetonitrile was removed from the obtained reaction liquid at 60° C. under a reduced pressure of 133 Pa, thereby obtaining a lithium borate derivative represented by the following formula.

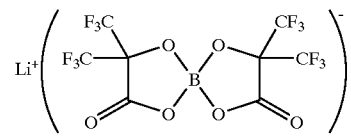

What is claimed is:
1. A process for synthesizing an ionic metal complex represented by formula (1), the process comprising:
reacting in an organic solvent a compound represented by formula (2) with a halogen-containing compound represented by formula (3) or (4), in the presence of a reaction aid comprising an element selected from the group consisting of elements of groups 1–4 and 11–14 of the periodic table, the reaction aid being a compound selected from the group consisting of chlorides, bromides, iodides, alkoxides, and carboxy compounds,

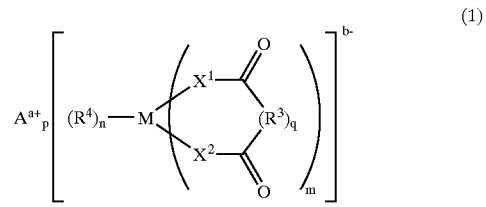

(1)

(2)

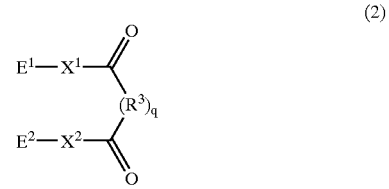

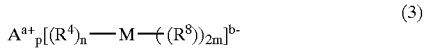

(3)

(4)

wherein M represents a transition metal selected from the group consisting of elements of groups 3–11 of the periodic table, or an element selected from the group consisting of elements of groups 12, 13 and 15 of the periodic table;
A$^{a+}$ represents a metal ion, hydrogen ion or onium ion;
a represents a number from 1 to 3; b represents a number from 1 to 3; p is b/a; m represents a number from 1 to 4; n represents a number from 0 to 8; q is 0 or 1;
R$^3$ represents a C$_1$–C$_{10}$ alkylene group, C$_1$–C$_{10}$ halogenated alkylene group, C$_4$–C$_{20}$ arylene group or C$_4$–C$_{20}$ halogenated arylene group, the alkylene and arylene groups of the R$^3$ optionally having substituents and hetero atoms, one of the R$^3$ being optionally bonded with another of the R$^3$;
R$^4$ represents a halogen, C$_1$–C$_{10}$ alkyl group, C$_1$–C$_{10}$ halogenated alkyl group, C$_4$–C$_{20}$ aryl group, C$_4$–C$_{20}$ halogenated aryl group or $X^2R^7$, the alkyl and aryl groups of the $R^4$ optionally having substituents and hetero atoms, one of the $R^4$ being optionally bonded with another of the $R^4$ to form a ring;

each of $X^1$, $X^2$ and $X^3$ independently represents O, S, $NR^5$ or $NR^5R^6$;

each of $R^5$, $R^6$ and $R^7$ independently represents a hydrogen, $C_1$–$C_{10}$ alkyl group, $C_1$–$C_{10}$ halogenated alkyl group, $C_4$–$C_{20}$ aryl group, or $C_4$–$C_{20}$ halogenated aryl group, the alkyl and aryl groups of the $R^5$ and $R^7$ optionally having substituents and hetero atoms, one of the $R^5$ being optionally bonded with another of the $R^5$ to form a ring, one of the $R^7$ being optionally bonded with another of the $R^7$ to form a ring;

each of $E^1$ and $E^2$ independently represents a hydrogen or alkali metal; and $R^8$ represents a halogen.

2. A process according to claim 1, wherein the reaction aid is a compound of an element selected from the group consisting of Al, B, Si, alkali metals and alkali earth metals.

3. A process according to claim 1, wherein the compound is $AlCl_3$, $BCl_3$ or $SiCl_4$.

4. A process according to claim 1, wherein the M is an element selected from the group consisting of Al, B, V, Ti, Zr, Cu, Y, Zn, Ga, Nb, Ta, Bi, P, As, Sc, Hf, and Sb.

5. A process according to claim 1, wherein the $A^{a+}$ is a lithium ion, quaternary alkylammonium ion or proton.

6. A process according to claim 1, wherein the $R^8$ is fluorine.

7. A process for synthesizing an ionic metal complex represented by formula (5), the process comprising:

reacting in an organic solvent a compound represented by formula (6) with a halogen-containing compound represented by formula (3) or (4), in the presence of a reaction aid comprising an element selected from the group consisting of elements of groups 1–4 and 11–14 of the periodic table, $$\left[A^{2+}_p\left[(R^4)_n-M\begin{pmatrix}X^1\diagup\overset{R^1}{\underset{(R^3)_q}{\overset{R^2}{C}}}\\O-C\\\parallel\\O\end{pmatrix}_m\right]^{b-}\right] \quad (5)$$

$$E^1-X^1-\overset{R^1}{\underset{(R^3)_q}{\overset{R^2}{C}}}\\E^2-O-C\\\parallel\\O \quad (6)$$

$$A^{a+}_p[(R^4)_n-M-((R^8))_{2m}]^{b-} \quad (3)$$

$$(R^4)_n-M-((R^8))_{2m-1} \quad (4)$$

wherein M represents a transition metal selected from the group consisting of elements of groups 3–11 of the periodic table, or an element selected from the group consisting of elements of groups 12, 13, and 15 of the periodic table;

$A^{a+}$ represents a metal ion, hydrogen ion or onium ion;

a represents a number from 1 to 3; b represents a number from 1 to 3; p is b/a; m represents a number from 1 to 4; n represents a number from 0 to 8; q is 0 or 1;

each of $R^1$ and $R^2$ independently represents a hydrogen, halogen, $C_1$–$C_{10}$ alkyl group, or $C_1$–$C_{10}$ halogenated alkyl group;

$R^3$ represents a $C_1$–$C_{10}$ alkylene group, $C_1$–$C_{10}$ halogenated alkylene group, $C_4$–$C_{20}$ arylene group or $C_4$–$C_{20}$ halogenated arylene group, the alkylene and arylene groups of the $R^3$ optionally having substituents and hetero atoms, one of the $R^3$ being optionally bonded with another of the $R^3$;

$R^4$ represents a halogen, $C_1$–$C_{10}$ alkyl group, $C_1$–$C_{10}$ halogenated alkyl group, $C_4$–$C_{20}$ aryl group, $C_4$–$C_{20}$ halogenated aryl group or $X^2R^7$, the alkyl and aryl groups of the $R^4$ optionally having substituents and hetero atoms, one of the $R^4$ being optionally bonded with another of the $R^4$ to form a ring;

each of $X^1$ and $X^2$ independently represents O, S, $NR^5$ or $NR^5R^6$;

each of $R^5$, $R^6$ and $R^7$ independently represents a hydrogen, $C_1$–$C_{10}$ alkyl group, $C_1$–$C_{10}$ halogenated alkyl group, $C_4$–$C_{20}$ aryl or $C_4$–$C_{20}$ halogenated aryl group, the alkyl and aryl groups of the $R^5$, $R^6$ and $R^7$ optionally having substituents and hetero atoms, one of the $R^5$ being optionally bonded with another of the $R^5$ to form a ring, one of the $R^6$ being optionally bonded with another of the $R^6$ to form a ring, one of the $R^7$ being optionally bonded with another of the $R^7$ to form a ring;

each of $E^1$ and $E^2$ independently represents a hydrogen or alkali metal; and $R^8$ represents a halogen.

8. A process according to claim 7, wherein the reaction aid is a compound of an element selected from the group consisting of Al, B, Si, alkali metals and alkali earth metals.

9. A process according to claim 8, wherein the compound is selected from the group consisting of chlorides, bromides, iodides, alkoxides and carboxy compounds.

10. A process according to claim 7, wherein the compound is $AlCl_3$, $BCl_3$ or $SiCl_4$.

11. A process according to claim 7, wherein the M is an element selected from the group consisting of Al, B, V, Ti, Zr, Cu, Y, Zn, Ga, Nb, Ta, Bi, P, As, Sc, Hf, and Sb.

12. A process according to claim 7, wherein the $A^{a+}$ is a lithium ion, quaternary alkylammonium ion or proton.

13. A process according to claim 7, wherein the $R^8$ is fluorine.

14. A process according to claim 1, wherein M represents a transition metal selected from the group consisting of elements of groups 3–11 of the periodic table, or an element selected from the group consisting of elements of groups 13 and 15 of the periodic table.

15. A process according to claim 14, wherein the M is an element selected from the group consisting of Al, B, V, Ti, Zr, Cu, Y, Ga, Nb, Ta, Bi, P, As, Sc, Hf, and Sb.

16. A process according to claim 1, wherein the M is an element selected from the group consisting of elements of groups 13 and 15 of the periodic table.

17. A process according to claim 16, wherein the M is an element selected from the group consisting of Al, B, Ga, Bi, P, As, and Sb.

18. A process according to claim 17, wherein the M is an element selected from the group consisting of B and P.

19. A process according to claim 7, wherein the M represents a transition metal selected from the group consisting of elements of groups 3–11 of the periodic table, or an element selected from the group consisting of elements of groups 13 and 15 of the periodic table.

20. A process according to claim 19, wherein the M is an element selected from the group consisting of Al, B, V, Ti, Zr, Cu, Y, Ga, Nb, Ta, Bi, P, As, Sc, Hf, and Sb.

21. A process according to claim 7, wherein the M represents an element selected from the group consisting of elements of groups 13 and 15 of the periodic table.

22. A process according to claim 21, wherein the M is an element selected from the group consisting of Al, B, Ga, Bi, P, As, and Sb.

23. A process according to claim 22, wherein the M is an element selected from the group consisting of B and P.

24. A process according to claim 1, wherein the reaction aid is a compound selected from the group consisting of chlorides, bromides, iodides, and carboxy compounds.

* * * * *